United States Patent [19]

Swan, Jr. et al.

[11] Patent Number: 4,681,606
[45] Date of Patent: Jul. 21, 1987

[54] DRIP CHAMBER

[75] Inventors: Jack C. Swan, Jr., Boulder, Colo.;
Paolo Poggioli, Mirandola, Italy

[73] Assignee: Cobe Laboratories, Inc., Lakewood, Colo.

[21] Appl. No.: 833,892

[22] Filed: Feb. 26, 1986

[51] Int. Cl.⁴ ............................................. B01D 19/00
[52] U.S. Cl. ........................................ 55/193; 55/201; 604/4
[58] Field of Search ................. 55/159, 190, 192, 193, 55/201; 210/188, 321.2; 604/4, 5, 122, 129, 321

[56] References Cited

U.S. PATENT DOCUMENTS

| | | | |
|---|---|---|---|
| 3,683,913 | 8/1972 | Kurtz et al. | 604/321 |
| 4,102,655 | 7/1978 | Jeffery et al. | 55/201 |
| 4,261,362 | 4/1981 | Kurtz et al. | 604/321 X |
| 4,287,059 | 9/1981 | Kume et al. | 210/188 |
| 4,428,743 | 1/1984 | Heck | 604/4 |
| 4,568,330 | 2/1986 | Kujawski et al. | 604/4 X |

FOREIGN PATENT DOCUMENTS

58325A1  2/1986  European Pat. Off. .

Primary Examiner—Charles Hart

[57] ABSTRACT

A flow-through chamber for conveying blood including an elongated container having sides, a top and a bottom for mounting with its longitudinal axis in a vertical orientation, an inflow tube formed integrally with the container, extending vertically along a side of the container and entering the container through a chamber inlet at a flow direction transverse to the longitudinal axis and at a location spaced from the bottom of the chamber, and an outflow tube formed integrally with the chamber, extending vertically along a side of the container and entering the container at its bottom at a chamber outlet.

6 Claims, 3 Drawing Figures

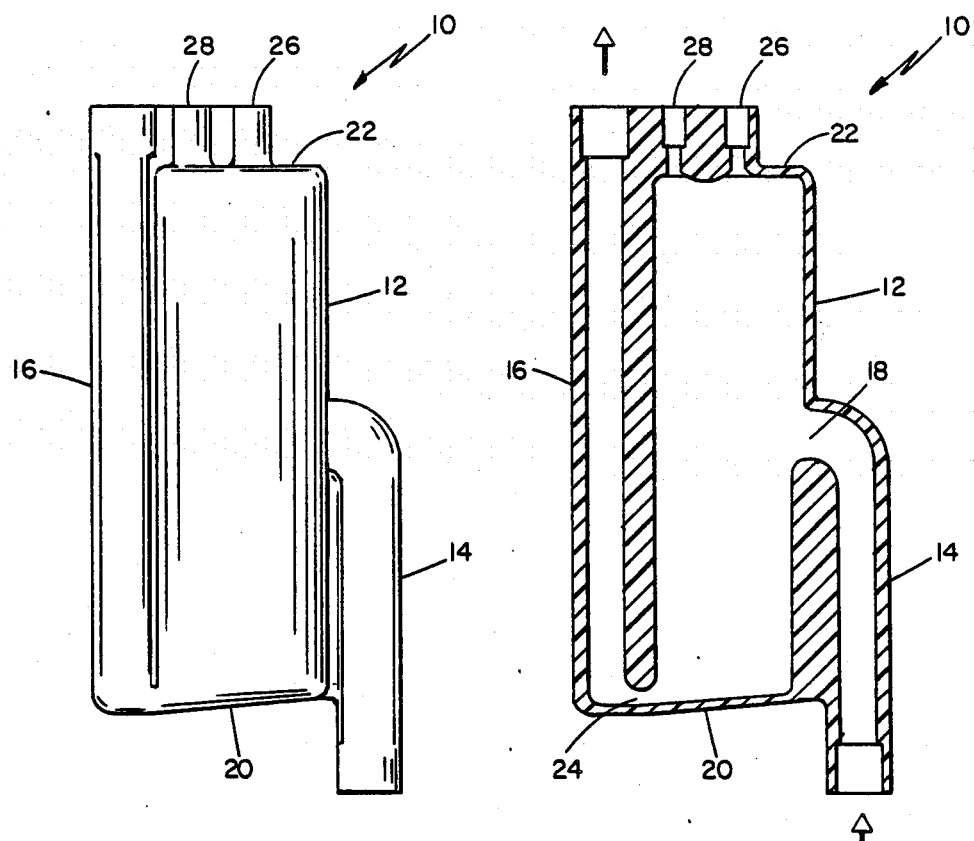

DRIP CHAMBER

FIELD OF THE INVENTION

The invention relates to removing gas bubbles from liquids such as blood that is withdrawn from the body for hemodialysis.

BACKGROUND OF THE INVENTION

When it has been desirable or necessary to remove gas bubbles from liquids flowing in closed systems, the art has employed devices known as bubble traps. One such need for a bubble trap has been removal of air bubbles from blood flowing extracorporeally through a dialyzer. A leak in the system where it is under negative pressure may cause such air bubble formation.

For example, Jeffery et al. U.S. Pat. No. 4,102,655 discloses a plastic bubble trap having a liquid inlet extending up through a container bottom and a liquid outlet extending downward through a container top, the outlet opening being lower in the container than the inlet opening. The top and the bottom are made of two injection molded polyvinyl chloride plastic pieces solvent bonded together. An additional opening in the top is connected to a pressure monitor.

A blood flow-through chamber used in a different application is shown in European Published Patent Application No. 0058325A1. This publication discloses a chamber made of blow molded plastic and having an inlet and an outlet near the bottom of the chamber and an indented side wall above the inlet to deflect the incoming fluid sideways to prevent frothing and to provide smooth flow. An outlet at the top of the chamber is for connection to a pressure monitor.

SUMMARY OF THE INVENTION

We have discovered that a desirable flow-through chamber for blood can be provided by an elongated container with integral inflow and outflow tubes connected to it, the inflow tube extending along a side of the container and entering the container at a chamber inlet at a flow direction transverse to the longitudinal axis of the container and at a location spaced from the bottom of the container, the outflow tube extending vertically along a side of the container and entering the container at its bottom at a chamber outlet.

In preferred embodiments the bottom of the container slopes toward the container outlet; the inflow tube enters the container at about half-way between the bottom and the top; there is a port for communicating with a pressure monitor at the top of the container; and the container and inflow and outflow tubes are made of blow molded plastic. Such a chamber is inexpensive to manufacture, requiring no assembly, and the blow molding process provides a smooth interior surface, which is desirable for conveying blood and avoids the rough edges of injection molded devices. Also, by directing the inflowing liquid to a point removed from the pressure monitoring port, the problem of spurts of blood entering the pressure monitoring port is avoided. The angled bottom of the container prevents stagnant regions.

Other advantages and features of the invention will be apparent from the following description of a preferred embodiment thereof and from the claims.

DESCRIPTION OF THE PREFERRED EMBODIMENT

The drawings will be briefly described.

DRAWINGS

FIG. 1 is an elevation of a flow-through chamber according to the invention.

FIG. 2 is a plan view of the FIG. 1 chamber.

FIG. 3 is a vertical sectional view, taken at 3—3 of FIG. 2, of the FIG. 1 chamber.

STRUCTURE

Referring to FIG. 1, there is shown blood drip chamber 10 made of blow-molded biocompatible polyvinyl chloride. Chamber 10 includes elongated container 12 for mounting with its longitudinal axis in a vertical orientation, integral inflow tube 14, and integral outflow tube 16. Elongated container 12 is approximately 1" in diameter and 3½" long. Inflow and outflow tubes 14 and 16 are approximately ⅜" in outer diameter and 0.160–0.220" in inner diameter.

Inlet tube 14 enters container 12 at chamber inlet 18 at a location at approximately half-way between container bottom 20 and container top 22. Outflow tube 16 enters container 12 at chamber outlet 24. Bottom 20 of container 12 slopes towards outlet 24 to the outflow tube 16. At the top of container 22 are inlet ports 26, 28 for connection to a pressure monitor and a tube for injecting liquids, e.g., heparin, respectively.

OPERATION

In operation, chamber 10 is connected to inflow and outflow tubes of a blood tubing set used, for example, with a dialyzer. Ports 26, 28 are similarly connected to tubes to a pressure monitor and an injection tube respectively. The tubes connected to inflow tube 14, outflow tube 16 and ports 26, 28 are solvent bonded.

Blood enters through inflow tube 14, travels vertically upward through it and is deflected sideways by the turn at inlet 18 to container 12. The blood then flows downward in container 12, at a reduced velocity owing to the increased flow area of container 12 compared to the flow area of tube 14, to outlet 24 to outflow tube 16. The blood flows upward through outflow tube 16. Blood typically fills container 12 to a level higher than inlet 18. The blood level is typically maintained by a manual air pump connected to port 26 with the pressure monitor.

Should a leak occur between where the blood is taken from the patient and inflow tube 14, air may enter the blood in the form of a bubble or bubbles, because of the negative pressure in the blood tubing. Blood or bubbles enter chamber 10 and are carried upward by the incoming blood flow toward the surface of the blood in container 12. Bubbles that reach the surface enter the gaseous atmosphere above the blood. Some bubbles may tend to be carried downward by the blood as it flows toward outlet 24, but because of the increase in cross-sectional area from inlet 18 to outlet 24, the blood flow downward is much slower, and there consequently is less drag on the bubbles and more opportunity for them to reach the surface, owing to their buoyancy.

Because the blood enters chamber 12 at a horizontal direction, any temporary spurts of blood are directed toward the opposite wall and not toward port 26 to the pressure monitoring device. Also, because the device is made by blow molding, as opposed to injection molding, there are very smooth interior surfaces, and these are less likely to cause damage to the platelets in the blood.

OTHER EMBODIMENTS

Other embodiments of the invention are within the scope of the following claims.

What is claimed is:

1. An in-line flow-through chamber for conveying blood comprising
   an elongated container having sides, a top and a bottom for mounting with its longitudinal axis in a vertical orientation,
   an inflow tube formed integrally with said container, extending upward vertically along a side of said container and entering said container through a chamber inlet at a flow direction transverse to said longitudinal axis and at a location spaced from the bottom of said chamber, and
   An outflow tube formed integrally with said chamber, extending vertically along a side of said container so that tubes attached to said inflow tube and said outflow tube are in line with each other, said outflow tube having its entrance at the bottom of said container and extending upward,
   said container providing a storage volume with uninhibited flow from said inflow tube to said outflow tube,
   said container including a port at the top of said container for communication with a pressure monitor, whereby said port is at a position spaced from the direction of flow of blood into said container to avoid directing spurts of blood to said port.

2. The chamber of claim 1 wherein said bottom of said container slopes toward said chamber outlet.

3. The chamber of claim 1 wherein said chamber inlet is about half-way between the bottom and the top of said container.

4. The chamber of claim 1 wherein said container also has a port at its top for supplying liquid to said container.

5. The chamber of claim 1 wherein said container and integral inflow tube and outflow tube are formed of blow molded plastic.

6. The chamber of claim 5 wherein said elongated container has a generally circular horizontal cross-section.

* * * * *